United States Patent
Shim et al.

(10) Patent No.: US 10,242,293 B2
(45) Date of Patent: Mar. 26, 2019

(54) METHOD AND PROGRAM FOR COMPUTING BONE AGE BY DEEP NEURAL NETWORK

(71) Applicants: The Asan Foundation, Seoul (KR); Vuno, Inc., Seoul (KR)

(72) Inventors: Woo Hyun Shim, Seoul (KR); Jin Seong Lee, Seoul (KR); Yu Sub Sung, Seoul (KR); Hee Mang Yoon, Seoul (KR); Jung Hwan Baek, Seoul (KR); Sang Ki Kim, Seoul (KR); Hyun Jun Kim, Gyeonggi-do (KR); Ye Ha Lee, Gyeonggi-do (KR); Kyu Hwan Jung, Seoul (KR)

(73) Assignees: The Asan Foundation, Seoul (KR); Vuno, Inc., Seoul (KR)

( * ) Notice: Subject to any disclaimer, the term of this patent is extended or adjusted under 35 U.S.C. 154(b) by 0 days.

(21) Appl. No.: 15/750,299

(22) PCT Filed: Dec. 30, 2015

(86) PCT No.: PCT/KR2015/014478
§ 371 (c)(1),
(2) Date: Feb. 5, 2018

(87) PCT Pub. No.: WO2017/022908
PCT Pub. Date: Feb. 9, 2017

(65) Prior Publication Data
US 2018/0232603 A1    Aug. 16, 2018

(30) Foreign Application Priority Data
Aug. 4, 2015    (KR) .................. 10-2015-0109822

(51) Int. Cl.
*G06K 9/62*    (2006.01)
*A61B 6/00*    (2006.01)
(Continued)

(52) U.S. Cl.
CPC .............. *G06K 9/6267* (2013.01); *A61B 5/00* (2013.01); *A61B 6/00* (2013.01); *G06K 9/4628* (2013.01);
(Continued)

(58) Field of Classification Search
CPC .. G06K 9/6267; G06K 9/6271; G06K 9/4628; G06K 9/66; G06K 2209/055;
(Continued)

(56) References Cited

U.S. PATENT DOCUMENTS

| 2018/0001184 A1* | 1/2018 | Tran | ..................... H04N 5/2257 |
| 2018/0165808 A1* | 6/2018 | Bagci | ..................... G06T 7/0012 |
| 2018/0232603 A1* | 8/2018 | Shim | ..................... A61B 6/00 |

FOREIGN PATENT DOCUMENTS

| CN | 107767376 | * | 3/2018 | ............... G06T 7/00 |
| JP | 2008-036068 A | | 2/2008 | |

(Continued)

OTHER PUBLICATIONS

Garn, Stanley M., et al. "Metacarpophalangeal length in the evaluation of skeletal malformation." Radiology 105.2 (1972): 375-381.

*Primary Examiner* — Jerome Grant, II
(74) *Attorney, Agent, or Firm* — Husch Blackwell LLP (57) ABSTRACT

Provided are a method and program for computing a bone age using a deep neural network. The method for computing a bone age using a deep neural network, including: receiving an analysis target image that is a specific medical image to compute the bone age; and analyzing the analysis target image by at least one computer using the deep neural network to compute the bone age. According to the present disclosure, since the bone age is computed by accumulating medical images of a specific race (particularly, Korean) and analyzing the same, it is possible to compute an accurate bone age that conforms to race.

18 Claims, 5 Drawing Sheets

(51) Int. Cl.
  *A61B 5/00*   (2006.01)
  *G06N 3/08*   (2006.01)
  *G06K 9/66*   (2006.01)
  *G06T 7/00*   (2017.01)
  *G06K 9/46*   (2006.01)

(52) U.S. Cl.
  CPC ............ *G06K 9/6271* (2013.01); *G06K 9/66* (2013.01); *G06N 3/08* (2013.01); *G06T 7/0014* (2013.01); *G06K 2209/055* (2013.01); *G06T 2207/10116* (2013.01); *G06T 2207/20081* (2013.01); *G06T 2207/20084* (2013.01); *G06T 2207/20182* (2013.01); *G06T 2207/30008* (2013.01)

(58) Field of Classification Search
  CPC ......... G06T 7/0014; G06T 2207/20182; G06T 2207/20084; G06T 2207/20081; G06T 2207/10116; G06T 2207/30008; A61B 6/00; A61B 5/00; G06N 3/08
  USPC ........................................................ 382/182
  See application file for complete search history.

(56) References Cited

FOREIGN PATENT DOCUMENTS

| | | | | |
|---|---|---|---|---|
| KR | 100715763 | B1 | 5/2007 | |
| KR | 100838339 | * | 6/2008 | ............... A61B 5/00 |
| KR | 100838339 | B1 | 6/2008 | |
| KR | 100864434 | B1 | 10/2008 | |
| KR | 1020140046156 | A | 4/2014 | |
| WO | WO2018057714 | * | 3/2018 | ............... A61B 6/00 |

* cited by examiner

METHOD AND PROGRAM FOR COMPUTING BONE AGE BY DEEP NEURAL NETWORK

CROSS REFERENCE TO RELATED APPLICATIONS

This application is a U.S. National Phase Application of International Application No. PCT/KR2015/014478 filed on Dec. 30, 2015, which claims the benefit of priority from Korean Patent Application 10-2015-0109822 filed on Aug. 4, 2015. The disclosures of International Application No. PCT/KR2015/014478 and Korean Patent Application 10-2015-0109822 are incorporated herein by reference.

TECHNICAL FIELD

The present disclosure relates to a method and program for computing bone age using a deep neural network, and more particularly, to a method and program for computing a patient's bone age by analyzing big data formed by accumulating medical images regarding a specific body part through a deep learning method using a deep neural network (DNN).

BACKGROUND ART

Assessment of bone age is one of the subjects frequently treated in pediatrics. The left hand of a child is imaged using X-Ray and the image is used to assess a bone age. The bone age assessment is an important indicator that can confirm whether a child develops normally. If there is a large discrepancy between an actual age and a measured bone age, it may be determined that there is an abnormality in bone growth (diabetes, genetic disease, etc.) and an appropriate treatment may be provided. A method for assessing a bone age from an X-ray image obtained by imaging the left hand includes Atlas and TW2 matching methods.

The Atlas matching method, which is proposed by Greulich and Pyle in the United States, evaluates a left hand radiographic image with a book containing radiographic images of the Atlas pattern group arranged according to age and sex. A physician will look at an image most similar to an overall shape of a child's X-ray image from the book of the Atlas pattern group to evaluate a bone age. Currently, 76% of physicians who evaluate bone age use this method. However, the Atlas matching method is highly likely to cause an error in the process of evaluating a bone age due to the degree of skill of a physician and a variation in bone growth of people.

Another method to assess a bone age is the TW2 method proposed by Tanner and Whitehouse in the UK. According to this method, each bone of the left hand is compared with the images in a book published by the TW2 group, rather than looking at the similarity of the whole image of the bone as in the Atlas matching method. Compared with the Atlas matching method in which similarity is analyzed in the whole image of the bone, in the TW2 method, individual bones are separately analyzed in features, and thus, a bone age can be more accurately measured, relative to the Atlas matching method. However, due to shortcomings in that it takes more time to evaluate a bone age, relative to the Atlas method, the TW2 method is not currently widely used.

According to the method of estimating a bone age using such Atlas or TW2, since a reading specialist evaluates a bone age by visually confirming the similarity of the image with naked eyes, the reliability of the bone age is degraded and much time is taken to estimate the bone age.

In order to solve such problem, Stanley M. Garn published a paper entitled "Metacarpophalangeal Length in the Evaluation of Skeletal Malformation" in 1972. This method, however, was limitedly used only in the white middle class as it simply attempted to measure a bone age by measuring only an absolute length of the bone.

INVENTION

Technical Problem

Books containing radiographic images of the Atlas pattern group are based on white people, and thus, they are not appropriate for non-white people. That is, a radiographic image based on the white standard cannot be used as an accurate standard for measuring a bone age of Korean children, and there is currently no comparative standard for bone age measurement appropriate for Koreans.

In addition, since the books containing radiographic images are made long ago, they cannot reflect a change in the pediatric development process according to the flow of time.

Moreover, since the conventional scheme performs comparison with images representing a specific bone age, if characteristics of several bone ages are included in an image of a specific pediatric patient, there is an ambiguity about how old the specific pediatric patient is to be determined.

Demand for a rapid and accurate bone age evaluation method which is programmatically implemented to overcome the unreasonableness of the conventional bone age evaluation methods is on the increase.

It is, therefore, an object of the present disclosure to provide a method and program for computing a bone age using a deep neural network, capable of forming a bone age determination criterion that conforms to race and age characteristics through analysis of a plurality of medical images (for example, radiographic images) using deep learning, and computing and providing an accurate bone age of a specific patient.

Technical Solution

According to one aspect of the present disclosure, there is provided a method for computing a bone age using a deep neural network, including: receiving an analysis target image that is a specific medical image to compute the bone age; and analyzing the analysis target image by at least one computer using the deep neural network to compute the bone age.

Further, the method may further include: recognizing a body part of the analysis target image.

Further, the analyzing the analysis target image may further include: generating training image data in which comparative images to be used in training by the deep neural network are accumulated, and wherein the comparative image may be a medical image in which a bone age of an imaged body part is determined to be normal by a medical staff.

Further, the comparative image may further include a medical image of an existing patient determined to have a specific bone age.

Further, the generating training image data may include: classifying the training image data based on a bone age to generate one or more groups; and computing a detailed feature through comparison between the groups.

Further, the generating training image data may further include: group-changing or excluding specific comparative images that are outside a range of the detail feature within each of the groups.

Further, the analyzing the analysis target image may include computing the bone age per sub-region in the body part imaged based on the detailed feature.

Further, the generating training image data may further include limiting a period range of the training image data to be used in training.

In addition, the method may further include indicating an identification mark in an area of the analysis target area corresponding to the detailed feature.

Further, the indicating an identification mark may include searching for the comparative image most similar to each area in which the identification mark is indicated, and providing it.

In addition, the method may further include providing a representative image corresponding to the computed bone age, wherein in the representative image may be an image designated by a medical staff as an image representative of a specific bone age.

Further, the at least one computer may include a representative image of each body part shape and recognizes a shape of a body part in the analysis target image to search for a representative image corresponding to the shape of the body part, and provide it.

Further, the number of representative images presented to correspond to the analysis target image may be adjusted based on the number of each person included in one or more groups obtained by classifying a total number of persons in which the specific body part is imaged, according to a specific classification criterion.

Further, the generating training image data may include generating a plurality of comparative augmented images by rotating or scaling the comparative image.

In addition, the method may further include generating a plurality of analysis target augmented images by rotating or scaling the analysis target image.

In addition, the method may further include deleting a portion corresponding to noise in the analysis target image.

In addition, the method of claim 11 may further include: receiving feedback data from a user based on the representative image or the analysis target image, wherein the feedback data is bone age data determined by the user; and correcting the bone age of at least one of the comparative images by reflecting the received feedback data.

According to another aspect of the present disclosure, there is provided a bone age computing program using a deep neural network, wherein the program is stored in a medium to execute the above-mentioned method in combination with a computer which is hardware.

Advantageous Effects

According to the present disclosure as described above, the following various effects may be achieved.

First, since a bone age is not determined based on white peoples 100 years ago but a medical image of a specific race (e.g. Korean) is accumulated as big data and analyzed to compute a bone age, it is possible to compute an accurate bone age that conforms to the race.

Second, since the medical image is established and used as big data, there is an advantage that more accurate bone age can be computed as the data accumulates.

Third, the accumulated big data is analyzed periodically or continuously through comparison, and when it is outside a range of common detained features of comparative images included in a specific group, it is excluded or group-changed, thereby making it possible to establish a more accurate bone age computation base.

Fourth, by limiting comparative images of a specific group to an appropriate time range in order to reflect a change in bone condition or growth rate of children according to the age change, it is possible to prevent an error in computing a bone age based on past data.

Fifth, according to an embodiment of the present invention, by analyzing the cumulative training image data, it is possible to generate a bone age determination criterion suitable for a specific race (for example, Korean).

BEST MODE

Hereinafter, preferred embodiments of the present disclosure will be described with reference to the accompanying drawings. The advantages and features of the present disclosure, and the method of achieving these will become apparent from the following description of embodiments, given in conjunction with the accompanying drawings. The present disclosure is not limited to the embodiments as set forth below but may be embodied in a variety of other forms. The present embodiments are merely provided to have a full understanding of the disclosure and to fully convey the scope of the disclosure to those skilled in the art to which the present disclosure belongs, and the present disclosure is only defined by the scope of the claims. Like reference numerals will refer to like elements throughout the disclosure.

Unless defined otherwise, all terms (including technical and scientific terms) used herein may be used in a sense that is commonly understood by people skilled in the art to which the present disclosure belongs. Further, the commonly used and predefined terms should not be abnormally or excessively interpreted unless explicitly defined otherwise.

The terms used herein are to illustrate the embodiments and are not intended to limit the scope of the disclosure. In the present disclosure, singular forms include plural forms unless the context clearly dictates otherwise. The terms "comprises" and/or "comprising" used herein do not exclude the presence or addition of one or more other elements, in addition to the stated elements.

In the present disclosure, a medical image refers to an image that may confirm bone state information of a patient obtained by various imaging methods. The imaging methods may include magnetic resonance imaging (MRI) imaging, as well as X-ray imaging using X-ray.

A computer used herein includes all various devices capable of performing computational processing to visually present results to a user. For example, the computer may be a smart phone, a tablet PC, a cellular phone, a mobile terminal of a personal communication service phone (PCS phone), a synchronous/asynchronous international mobile telecommunication-2000 (IMT-2000), a palm personal computer (palm PC), and a personal digital assistant (PDA) or the like, as well as a desktop PC or a laptop computer. The computer may also be a medical device that acquires or observes medical images. In addition, the computer may be a server computer connected to various client computers.

In the present disclosure, a deep neural network (DNN) refers to a system or network in which one or more layers are established in one or more computers to perform determination based on a plurality of data. For example, the deep neural network may be implemented as a set of layers including a convolutional pooling layer, a locally-connected layer, and a fully-connected layer. The convolutional pulling layer or locally-connected layer may be configured to extract features in an image. The fully-connected layer can determine a correlation between image features. In some embodiments, the overall structure of the deep neural network may have a convolutional neural network (CNN) structure that the locally-connected layer is connected to a convolutional pulling layer and the fully-connected layer is connected to the locally-connected layer. Further, the deep neural network may have a recurrent neural network (RNN) structure which is connected in a recursive manner, for example, by including edges pointing to the nodes of each layer themselves. The deep neural network may include various determination criteria (i.e., parameters) and may add new determination criteria (i.e., parameters) through input image analysis.

In the present disclosure, an analysis target image (or an image to be analyzed) refers to a medical image input to a deep neural network implemented by one or more computers to compute a bone age. Further, in the present disclosure, a comparative image refers to a medical image in which common features are accumulated and analyzed to compute a bone age of the analysis target image. In addition, training image data refers to accumulated data obtained by accumulating the comparative image. Further, in the present disclosure, a representative image refers to an image designated by a medical staff as an image representative of a specific bone age.

In the present disclosure, a detailed feature refers to a common feature of a comparative image within a specific bone age group derived through analysis of training image data. For example, the detailed feature may include a length of a specific bone of a specific body part, a shape of a connection portion between adjacent bones, and the like. A plurality of detailed features may be accumulated and used as a determination criterion for computing a bone age. In addition, in the present disclosure, a detailed area refers to an area corresponding to a specific detailed feature within a medical image regarding a specific body part.

Figure 1:
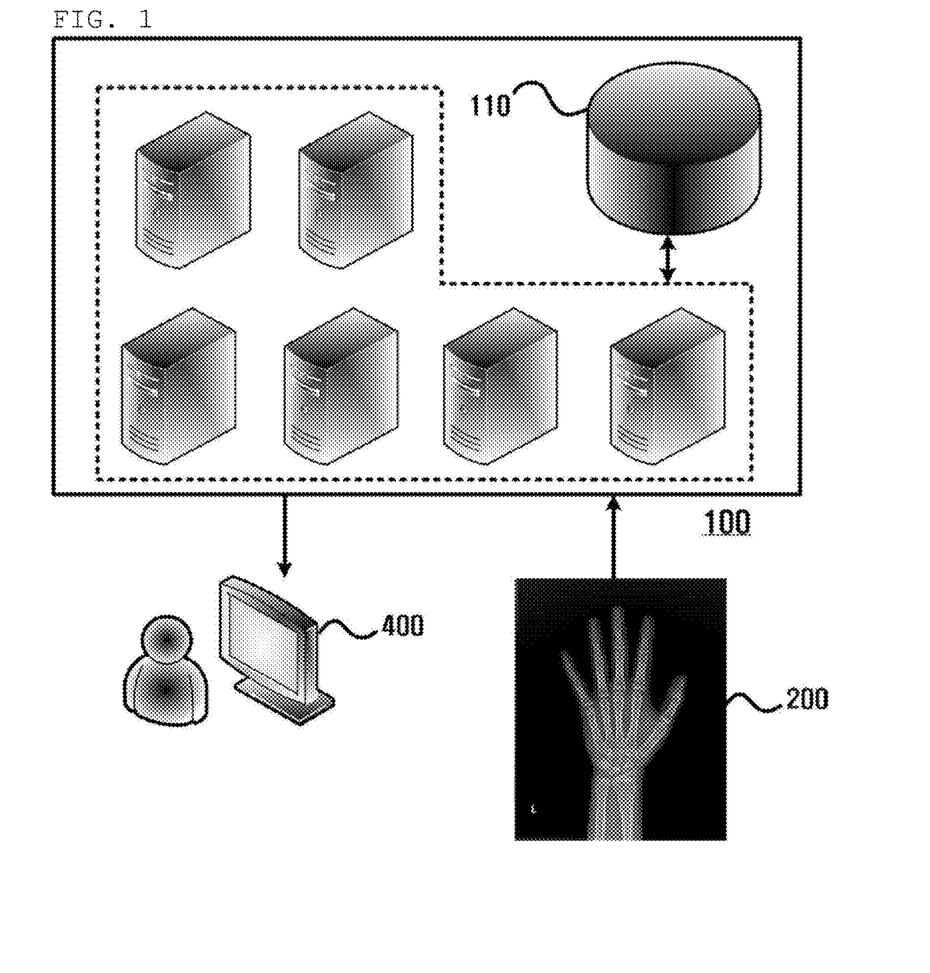
FIG. 1 is a configuration diagram of a bone age computing system according to an embodiment of the present disclosure.
Figure 2:
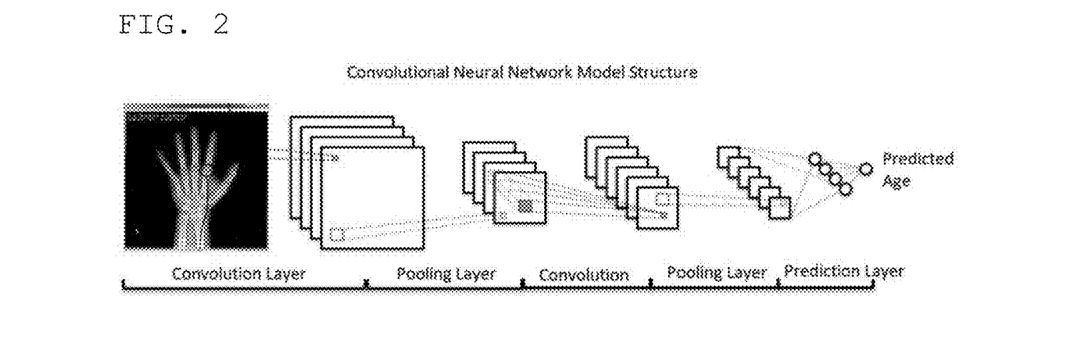
FIG. 2 is a diagram illustrating a connection structure within a deep neural network according to an embodiment of the present disclosure.
Figure 3:
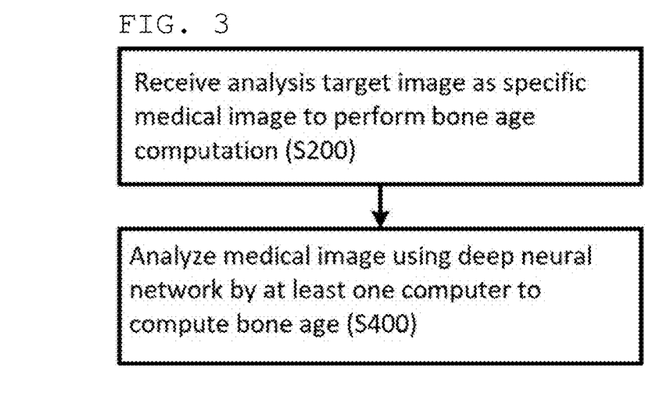
FIG. 3 is a flow chart illustrating a bone age computing method using the deep neural network according to an embodiment of the present disclosure.
Figure 4:
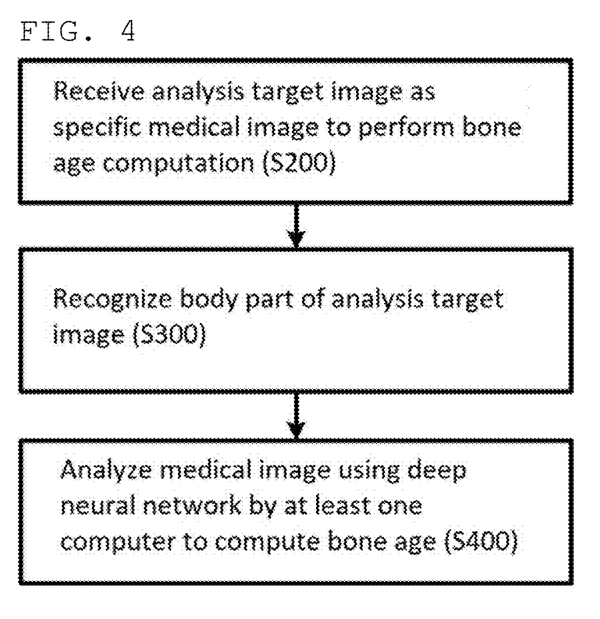
FIG. 4 is a flow chart illustrating a bone age computing method using a deep neural network in which one or more computers recognize a body part of an analysis target image according to an embodiment of the present disclosure.
Figure 5:
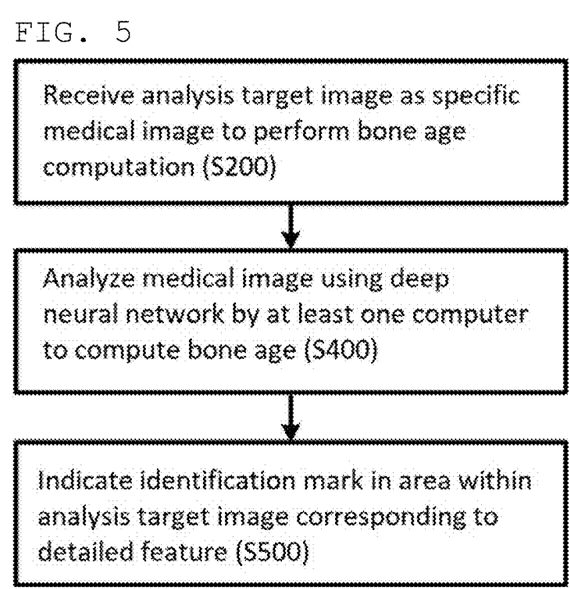
FIG. 5 is a flow chart illustrating a bone age computing method using a deep neural network in which an identification mark is indicated in detailed features of the analysis target image along with a result of bone age computation according to an embodiment of the present disclosure.
Figure 6:
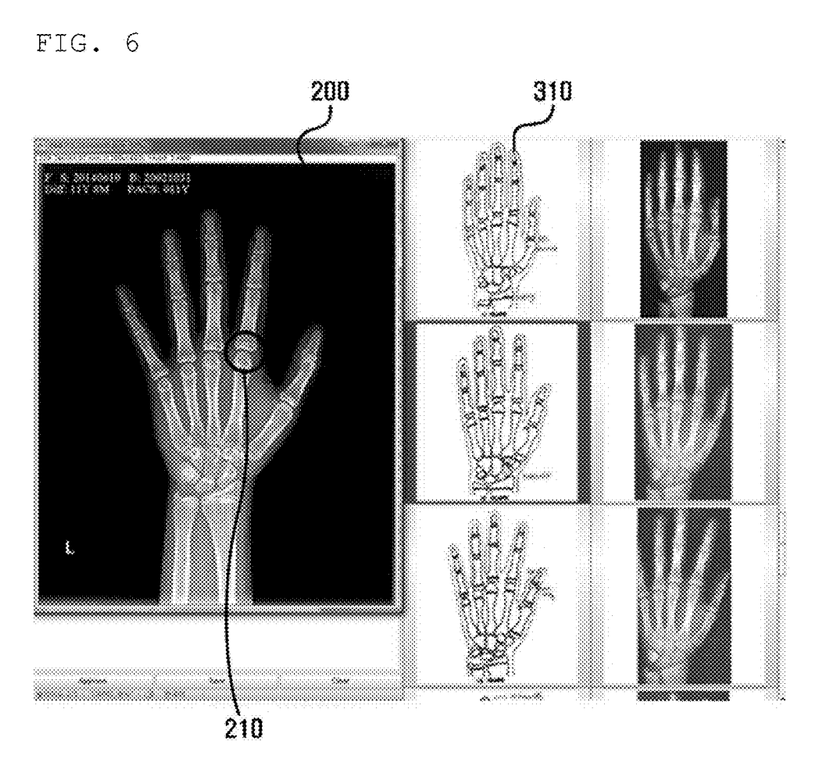
FIG. 6 is an example diagram illustrating an analysis target image and comparative images displayed on a screen according to an embodiment of the present disclosure.

FIG. 1 is a configuration diagram of a bone age computing system according to an embodiment of the present disclosure. FIG. 2 is a diagram illustrating a connection structure within a deep neural network according to an embodiment of the present disclosure. FIG. 3 is a flow chart illustrating a bone age computing method using the deep neural network according to an embodiment of the present disclosure. FIG. 4 is a flow chart illustrating a bone age computing method using a deep neural network in which one or more computers recognize a body part of an analysis target image according to an embodiment of the present disclosure. FIG. 5 is a flow chart illustrating a bone age computing method using a deep neural network in which an identification mark is indicated in detailed features of the analysis target image along with a result of bone age computation according to an embodiment of the present disclosure. FIG. 6 is a diagram illustrating an analysis target image and comparative images displayed on a screen according to an embodiment of the present disclosure.

FIGS. 1 to 6 illustrate a bone age computing system 100, an analysis target image 200, an identification mark 210, training image data 300, a comparative image 310, and an output device 400.

Hereinafter, a method and program for computing a bone age using a deep neural network according to embodiments of the present disclosure will be described with reference to the accompanying drawings.

The embodiments of the present disclosure are directed to a system for implementing a bone age computing method using a deep neural network (hereinafter, referred to as a bone age computing system), which may be implemented in one computer or in a plurality of computers connected to each other through a network. For example, as in FIG. 1, the bone age computing system may include at least one computer 100 and an output device 400. The at least one computer may include a database server 110 that includes training image data. The at least one computer 100 may receive an analysis target image 200 and compare the analysis image 210 with training image data 210 in the database server 110 to compute a bone age and provide it to the output device 400. For example, the bone age computing system may also be implemented by a single computer, and thus, it may store the training image data 300 in a memory (e.g., a hard disk) of the computer, acquire the analysis target image 200, and compares it with the training image data 300 to compute a bone age.

The deep neural network according to the embodiments of the present disclosure may have a structure called a convolutional neural network appropriate for image analysis as illustrated in FIG. 2. The convolutional neural network may have a structure in which a feature extraction layer which learns a feature with greatest discrimination power from given image data by itself and a prediction layer which learns a prediction model to exhibit highest prediction performance based on an extracted feature are integrated.

The feature extraction layer may have a structure in which a convolution layer that creates a feature map by applying a plurality of filters to each area of an image and a pooling layer that enables to extract a feature which is not changed over a change in position or rotation by spatially integrating the feature map are alternately repeated several times. This enables extraction of various levels of features from a low-level feature such as a point, a line, a surface or the like to a complex and meaningful high-level feature.

The convolution layer obtains a feature map by taking a nonlinear activation function to a filter and an inner product of a local receptive field for each patch of an input image. Compared with other network structure, CNN features that it uses a filter having shared weights and sparse connectivity. This connection structure reduces the number of parameters to be trained and makes training through back propagation algorithm efficient, resulting in improved prediction performance.

The pooling layer (or sub-sampling layer) creates a new feature map by utilizing area information of the feature map obtained from a previous convolution layer. In general, the feature map newly created by the pooling layer is reduced to a size smaller than the original feature map and a representative integration method includes maximum pooling to select a maximum value of a corresponding area in the feature map and average pooling to obtain an average value of the corresponding area in the feature map. The feature map of the pooling layer may generally be less affected on a certain structure or a position of a pattern present in the input image, relative to a feature map of a previous layer. That is, the pooling layer may extract features robust to a local change such as noise or distortion in the input image or the previous feature map, and such a feature may play an important role in classification performance. Another role of the pooling layer is to reflect a feature of a wider area as it goes from a deep structure to an upper learning layer. As the feature extraction layer accumulates, a feature that reflects a local feature in a lower layer and reflects a feature of the entire abstract image toward an upper layer may be created.

Like a classification model such as a multi-layer perception (MLP) or a support vector machine (SVM), the features finally extracted through repetition of the convolution layer and the pooling layer as described above are combined to each other, so as to be used for classification model training and prediction.

However, the structure of the deep neural network according to the embodiments of the present disclosure is not limited thereto and may be formed as a neural network having various structures.

FIG. 3 is a flow chart illustrating a bone age computing method using the deep neural network according to an embodiment of the present disclosure.

Referring to FIG. 3, the bone age computing method using the deep neural network according to an embodiment of the present disclosure includes receiving an analysis target image 200 as a specific medical image for performing bone age computation (S200) and analyzing the medical image using the deep neural network by at least one computer 100 to compute a bone age (S400). The bone age computing method using the deep neural network according to an embodiment of the present disclosure will be described in order.

The bone age computing system receives the analysis target image 200 (S200). The analysis target image 200 corresponds to a specific medical image to be subjected to bone age computation. The at least one computer 100 establishing the bone age computing system may load the specific analysis target image 200 stored therein. For example, the at least one computer 100 may retrieve a medical image regarding a particular body part of a specific patient captured by a medical imaging device and stored therein. Further, the at least one computer 100 may directly receive the captured analysis target image 200 from the medical imaging device. In addition, when the at least one computer 100 is the medical imaging device, the computer may acquire the analysis target image 200 by capturing a body part of a specific patient.

The at least one computer 100 analyzes the analysis target image 200 using the deep neural network to compute a bone age (S400). For example, the at least one computer 100 may perform image comparison based on a plurality of medical images established as big data and search for a similar comparative image 310 or a corresponding image group. A bone age corresponding to the searched comparative image 310 or the image group may be computed as a bone age of the specific patient.

The bone age computing step (S400) may include generating training image data 300 in which the comparative image 310 to be used in training by the deep neural network is accumulated. The deep neural network implemented by the at least one computer 100 is required to learn a plurality of images corresponding to big data in order to compute a bone age. To this end, the at least one computer 100 should accumulate a plurality of medical images (i.e., comparative images 310) for learning a bone age computation criterion or computation method.

The at least one computer 100 may extract a medical image captured for inspection when a patient visits a hospital, to establish a database corresponding to the training image data 300. For example, when the patient visits the hospital due to a sore wrist or finger, the patient is imaged by an X-ray. Medical images regarding specific body parts of the hospital visitor are accumulated to form big data. In particular, medical images of a child as a target of bone age computation may be accumulated to establish big data to be utilized for bone age computation.

In addition, in step of generating the training image data 300, the at least one computer 100 may classify or extract a medical image in which a body part imaged as the comparative image 310 included in the training image data 300 is determined to be normal, and accumulate the same. The medical image determined to be normal may include a medical image of a person whose medial image (for example, radiography (X-ray film) image) has been captured for medical examination but determined without abnormality by the medical staff. Also, the medical image determined to be normal may include a medical image of a specific body part acquired while capturing the medical image due to a disease of another body part. For example, since a hand image obtained, while performing radiographing due to a wrist fracture, may be determined as a normal image, the at least one computer 100 may determine that a bone age of the person is normal, and extract the training image data 300. In the medical image determined to be normal, a bone age may be determined based on a birth date of the testee.

Furthermore, the comparative image 310 may further include a medical image of an existing patient determined to have a specific bone age. For example, when the growth of a child is determined to be faster or slower than a normal speed and thus x-ray is taken for bone age measurement, the medical image (i.e., radiographic image) of the testee may be determined to have a specific bone age. In particular, when the system according to an embodiment of the present disclosure is established, a specific bone age is computed regarding a medical image of patients analyzed through comparison with the previously accumulated bone age image and added to the training image data 300. Thus, the bone age measuring system has an advantage that a large number of data of the comparative image 310 that may be analyzed may be secured.

Further, the training image data 300 generating step may include classifying the training image data 300 based on a bone age to generate one or more groups; and computing a detailed feature of each group. That is, the at least one computer 100 may classify the accumulated comparative images 310 based on a bone age to form one or more groups. Thereafter, the at least one computer 100 may search for the detailed feature within each group. The detained feature may include a length of a specific bone of a specific body part, a shape of a connection portion between adjacent bones, and the like.

In an embodiment of a method for computing a detailed feature within a group, the at least one computer 100 may compare medical images of a specific group and search for a common feature included in the medical images (or comparative images 310) of the same group. In another embodiment, the at least one computer 100 may recognize a changed portion between the classified groups and recognize a detailed feature. Specifically, the at least one computer 100 may sequentially sort the classified groups according to the growth process of the children (i.e., in order of bone age) and perform comparison between groups at adjacent times, and thus, recognize a detailed feature changing according to age.

Accordingly, in the bone age computation step (S400), a bone age per sub-region in the body part imaged based on the detailed feature may be computed. That is, the at least one computer 100 may utilize the detailed feature computed according to the detailed feature computing method as described above as a determination criterion for computing a bone age of the analysis target image 200. Since the detailed feature of each group derived through the analysis of the comparative image 310 (i.e., the training image data 300) established by the big data correspond to a specific bone age criterion, the at least one computer 100 may set the derived detailed feature as a bone age determination reference.

In addition, the at least one computer 100 may compute the frequency or rate at which one or more detailed features included in the specific group appear in the comparative image 310 within the group. That is, since a single medical image may include features of various bone ages, priority or importance may be determined when determining a bone age based on a rate of appearance of each detailed feature in the comparative image 310 within the specific bone age group.

In addition, the training image data 300 generating step may further include group-changing or excluding a specific comparative image 310 which is outside the range of the detailed features in each group. That is, a plurality of comparative images 310 included in a specific group are compared with each other, and when a specific comparative image 310 is outside the range that may be determined as the detailed feature of the group, the at least one computer 100 may exclude the comparative image 310 which is outside the range from the group, and when the comparative image 310 is determined to include a detailed feature of another group, the at least one computer 100 may perform group change. Accordingly, a detailed feature of each group may be clarified by determining whether it is proper to include the specific comparative image 310 in the group continuously in the process of accumulating the comparative image 310, thereby accurately determining a bone age of the specific analysis target image 200.

Further, in step of generating the training image data 300, the at least one computer 100 may classify the acquired medical images by body parts. For example, the at least one computer 100 may classify the obtained medical images based on an input reference image of each body part, and the at least one computer 100 may recognize a body part according to unsupervised learning by itself without any input of a separate reference image. Also, for example, at least one computer 100 may determine a body part corresponding to the medical image based on text data (e.g., a result of reading a specific medical image) matching each medical image. Thereafter, the at least one computer 100 may store the medical image in which the body part is identified in a per-body part database.

In addition, in step of generating the training image data 300, a period range of the training image data 300 to be used in training may be limited. According to the changes of the times, a physical condition or growth rate of children varies by ages. Therefore, an old-established medical image may serve as an error in computing a bone age of the current standard. Accordingly, the at least one computer 100 may compare the comparative images 310 included in the specific group in order of imaged time, determine a point at which a determination criterion of the detailed feature is clarified, and utilize only a subsequent medical image as the training image data 300.

In addition, as illustrated in FIG. 4, the method may further include recognizing a body part of the analysis target image 200 (S300). That is, the at least one computer 100 may recognize a body part by analyzing the received analysis target image 200. The at least one computer 100 may recognize a corresponding body part based on the reference image of each body part or the feature information of each body part recognized through analysis of the prestored comparative image 310, or recognize the body part by itself according to unsupervised learning without input of the separate reference image or without a result of analyzing the prestored comparative image 310. Accordingly, the at least one computer 100 may limit the range of the comparative image 310 to be recognized for bone age computation, thereby increasing a bone age computation speed.

In addition, as illustrated in FIG. 5, the method may further include indicating the identification mark 210 in an area of the analysis target image 200 corresponding to the detailed feature (S500). That is, the at least one computer 100 may display the analysis target image 200 together for the user, while calculating and providing the bone age. Further, as illustrated in FIG. 6, the at least one computer 100 may indicate the identification mark 210 corresponding to the detailed feature in the analysis target image 200. Accordingly, the user may check by which detailed feature the at least one computer 100 have computed the analysis target image 200 as the corresponding bone age.

The identification mark 210 indicating step (S500) may further include searching for the comparative image 310 most similar to an area in which each identification mark 210 is indicated, and providing it. That is, the at least one computer 100 may extract the comparative image 310 including a detailed feature included in the analysis target image 200 and provide it to the user. If several detailed features included in one analysis target image 200 are detailed features included in different bone ages, the at least one computer 100 may match the comparative image 310 corresponding to each detailed feature within the analysis target image 200 and provide it. The at least one computer 100 may display the analysis target image 200 together while displaying the searched comparative image 310 on a screen, and may display a corresponding comparative image 310 on the screen when receiving a designated area corresponding to each detained feature.

In addition, the at least one computer 100 may receive and store a representative image for each bone age set by the medical staff. The representative image refers to an image designated by the medical staff as an image representative of a specific bone age. That is, the at least one computer 100 may include one or more representative image groups. The representative image groups (or representative image sets) may be classified by body part shapes (e.g., hand shape), genders, and ages and stored in the computer 100. For example, the analysis target image 200 may be captured in various hand shapes depending on imaging situations or imaging purposes. Thus, in order for the medical staff to clarify and easily confirm the results computed through deep learning, the at least one computer 100 is required to search for a representative image similar to a hand shape of the analysis target image 200 and provide the same. Accordingly, the at least one computer may receive a designated representative image from the medical staff according to the hand shape even for the same bone age.

To this end, the at least one computer 100 may recognize a hand shape included in the analysis target image and select a most matching bone age image group by hand shapes. For example, the at least one computer 100 may extract a representative image group matching the hand shape of the analysis target image 200 and select a representative image for each bone age including the same detailed feature as that of the analysis target image 200 from among a plurality of representative images included in the representative image group for each hand shape.

The at least one computer 100 may display the analysis target image 200 and the selected representative image together on a screen. For example, the at least one computer 100 may display the representative image and the analysis target image 200 side by side or in an overlapping manner. Accordingly, since the at least one computer 100 displays the representative image set by the medical staff together, as well as the comparative image computed through deep learning, increasing the reliability of the bone age computation result.

In addition, the at least one computer 100 may adjust the number of representative images presented to correspond to an analysis target based on the number of persons included in one or more groups formed by classifying a total number of imaged persons (i.e., population) according to a specific classification criterion. The classification criteria may be age, sex, area, and the like. In addition, the at least one computer 100 may adjust the number of representative images based on the accuracy (i.e., an accurate probability value of bone age to be computed) of computation of the bone age expected according to the number of persons included in each group, as well as adjusting the number of representative images according to the number of persons included in each group.

In an embodiment, the at least one computer 100 may adjust the number of representative images presented to correspond to the analysis target image based on the number of persons of a group corresponding to an age of a patient captured for the analysis target image 200 based on age used as a classification criterion. That is, since the number of patients to be imaged is different according to age, in the case of age having a large number of comparative images, a bone age may be accurately computed through deep learning to present a small number of representative images. On the other hand, if the number of comparative images is small, since a result computed through deep learning may be inaccurate, a large number of representative images may be presented.

For example, in case where toddlers between 1 and 10 years of age are subject to be imaged by X-ray, the number of toddlers to be imaged from 4 to 8 years of age is large, and thus, the accuracy of patients in this age may be high, and data of 1 and 2 years of age or 9 and 10 years of age is relatively less, obtaining a result of low probability. Thus, if a 6-year-old is taken, since it is a section with very high reliability, only two or three sheets of result according to probability may be shown, and when 1-year-old is taken, since the reliability is low, more results (e.g., five to eight sheets) are shown accordingly to help the medical staff determine and reduce mistake of the medical staff.

The method may further include augmenting the analysis target image or the comparative image to perform deep learning. If the directions and/or sizes of the analysis target image and the comparative image are not matched, the at least one computer 100 may not compute an accurate bone age by comparing the analysis target image with the comparative image.

In an embodiment, the at least one computer 100 may generate a plurality of analysis target augmented images by rotating the analysis target image in various directions or scaling (i.e., enlarging or reducing) it. The computer may compare each of the analysis target augmented images with a plurality of comparative images, extract a comparative image with highest similarity, and compute a similarity with each comparative image. As a result, the at least one computer may compute a bone age of the comparative image having the highest similarity to the specific analysis target augmented image as a result.

In another embodiment, the at least one computer 100 may augment the comparative image stored by rotating the comparative image in various directions or adjusting the size (i.e., magnifying or reducing) (that is, a plurality of comparative augmented images are generated). Accordingly, since the at least one computer 100 store the comparative images in various shooting directions and having various sizes, the at least one computer 100 may rapidly compute an accurate bone age directly using the acquired analysis target image 200 without any modification or manipulation of the acquired analysis target image 200.

In addition, the at least one computer may further include deleting a portion corresponding to noise in the analysis target image. The portion corresponding to noise refers to an area within the analysis target image unnecessary for computation of bone age. For example, when radiography is taken on a body part of a toddler, a caregiver or a medical staff may be imaged together, while they hold the child's body part for accurate photographing. At this time, the body part of the caregiver or the medical staff may be included in the analysis target image as a portion corresponding to noise. In order for the at least one computer 100 to accurately compute a bone age of the body part included in the analysis target image 200, it is necessary to delete the body part of the parent or medical staff, which is an unnecessary area, from the analysis target image.

In an embodiment of a method of deleting the portion corresponding to noise, a scheme of deleting the portion other than the imaging area from the analysis target image may be applied. For example, the at least one computer 100 may delete an area outside a specific range from the center of the analysis target image 200. That is, when the analysis target image 200 is captured, the body part as a bone age computation target will be positioned at the center, and thus, the at least one computer may determine an image included in an area outside the specific range from the center as a portion corresponding to noise and delete the same. In addition, for example, the at least one computer 100 may receive a body part corresponding to a target to be imaged from the user (e.g., the medical staff), recognize the corresponding body part included in the analysis target image 200, and delete a target included in other area.

In addition, the at least one computer 100 may receive feedback data from the user (e.g., the medical staff) and perform re-learning. Since the bone age result computed through deep learning may not be accurate, the at least one computer 100 may receive feedback from the medical staff as to whether the presented comparative image or representative image is appropriate.

In an embodiment, when the bone age finally determined by the medical staff is different from the deep learning computation result, the at least one computer 100 may receive the bone age determined by the medical staff. That is, when there is an error between the bone age predicted through the deep learning algorithm and the bone age determined by the medical staff by a threshold value or greater, the at least one computer may learn the bone age determined by the medical staff to increase the accuracy of the bone age computation algorithm (i.e., a deep learning algorithm).

For example, the at least one computer 100 may correct the bone age of the comparative image used for bone age computation through the feedback data received from the user based on the representative image or the analysis target image provided to the user (for example, a medical staff). In addition, for example, the at least one computer 100 may add the analysis target image, which has been finally determined by the doctor, to the comparative image group of the finally determined bone age. Accordingly, the bone age of the already stored comparative image may be accurately corrected in consideration of the determination of the medical staff and a new comparative image in which the bone age is accurately determined by the medical staff may be added, thereby increasing the accuracy of the bone age computation of the analysis target image.

The at least one computer may obtain feedback data from the medical staff in various manners. For example, the at least one computer may receive the bone age value of the analysis target image directly from the medical staff, and indirectly receive the bone age by selecting a representative image that is the closest to the plurality of representative images provided to the medical staff. The method of receiving the feedback data is not limited thereto and various methods may be applied.

The bone age computing method using the deep neural network according to an embodiment of the present disclosure described above may be implemented as a program (or application) to be executed in combination with a computer which is a hardware, and stored in a medium.

The program described above may include a code encoded in a computer language such as C, C++, JAVA, a machine language or the like that may be read by a processor (CPU) of the computer through a device interface of the computer, in order to cause the computer to read the program and execute the methods implemented in the program. This code may include functional codes related to functions or the like that define the necessary functions for executing the methods and include control codes related to the execution procedures necessary to cause the processor of the computer to execute the functions in a predetermined procedure. In addition, the code may further include a memory reference related code for additional information or media necessary to cause the processor of the computer to perform the functions, as to which location (address) of the computer's internal or external memory should be referenced. Further, when the processor of the computer needs to communicate with any other computer or server remotely to perform the functions, the code may include a communication related code as to whether how to communicate with any other computer or server remotely using the communication module of the computer or which information or media should be transmitted or received during communication.

The stored medium is not a medium for storing data for a short time such as a register, a cache, a memory or the like, but refers to a medium which semi-permanently stores data and is capable of being read by a device. Specifically, examples of the stored medium include ROM, RAM, CD-ROM, a magnetic tape, a floppy disk, an optical data storage, and the like, but are not limited thereto. That is, the program may be stored in various recording media on various servers accessible by the computer, or on various recording media on the user's computer. In addition, the medium may be distributed over a network-connected computer system, and a computer-readable code may be stored in a distributed manner.

While certain embodiments have been described, these embodiments have been presented by way of example only, and are not intended to limit the scope of the disclosures. Indeed, the embodiments described herein may be embodied in a variety of other forms. Furthermore, various omissions, substitutions and changes in the form of the embodiments described herein may be made without departing from the spirit of the disclosures. The accompanying claims and their equivalents are intended to cover such forms or modifications as would fall within the scope and spirit of the disclosures.

What is claimed is:

1. A method for computing a bone age using a deep neural network, comprising:
   receiving, by a communication module of at least one computer, an analysis target image that is a specific medical image to compute the bone age; and
   analyzing the analysis target image which is received via the communication module, by a processor of the at least one computer, using the deep neural network to compute the bone age, wherein the analysis target image is of bones of entire hand, and
   wherein the deep neural network includes a plurality of convolution layers which create a feature map with respect to features in the analysis target image; and a pooling layer in which a sub-sampling is performed between the plurality of convolution layers, whereby different levels of features are extracted.

2. The method of claim 1, further comprising recognizing, by the processor, the bones of hand of the analysis target image.

3. The method of claim 1, further comprising generating, by the processor, a plurality of analysis target augmented images by rotating or scaling the analysis target image.

4. The method of claim 1, further comprising deleting, by the processor, a portion corresponding to noise in the analysis target image.

5. The method of claim 1, further comprising providing, by the processor, a representative image corresponding to the computed bone age,
   wherein in the representative image is an image designated by a medical staff as an image representative of a specific bone age.

6. The method of claim 5, wherein a representative image of bones of hand is stored by a memory of the computer and the processor of the computer recognizes a shape of bones of hand in the analysis target image to search for a representative image corresponding to the shape of the bones of hand, and provides it.

7. The method of claim 5, wherein the number of representative images presented to correspond to the analysis target image is adjusted based on the number of persons included in one or more groups obtained by classifying a total number of persons in which bones of hand are imaged, according to a specific classification criterion.

8. The method of claim 5, further comprising:
a feedback data receiving step of receiving, by the communication module, feedback data from a user based on the representative image or the analysis target image, wherein the feedback data is bone age data determined by the user; and
correcting, by the processor, the bone age of at least one comparative image by reflecting the feedback data received by the communication module.

9. The method of claim 1, wherein the analyzing the analysis target image further includes:
generating, by the processor, training image data in which comparative images to be used in training by the deep neural network are accumulated, and
wherein the comparative image is a medical image in which a bone age of an imaged bones of hand is determined to be normal by a medical staff.

10. The method of claim 9, wherein the comparative image further includes a medical image of an existing patient determined to have a specific bone age.

11. The method of claim 9, wherein the generating training image data includes:
classifying, by the processor, the training image data based on a bone age to generate one or more groups; and
computing, by the processor, a detailed feature through comparison between the generated groups.

12. The method of claim 11, wherein the generating training image data further includes:
group-changing or excluding, by the processor, a specific comparative image which is outside a range of the detailed feature within each of the groups.

13. The method of claim 11, further comprising indicating, by the processor, an identification mark in an area of the analysis target area corresponding to the detailed feature.

14. The method of claim 13, wherein the indicating an identification mark includes searching, by the processor, for the comparative image most similar to each area in which the identification mark is indicated, and providing it.

15. The method of claim 9, wherein the generating training image data is characterized in that a period range of the training image data to be used in training is limited.

16. The method of claim 9, wherein the generating training image data includes generating, by the processor, a plurality of comparative augmented images by rotating or scaling the comparative image.

17. A bone age computing program using a deep neural network, wherein the program is stored in a medium and includes instructions implemented to cause a computer, which is hardware, to execute the method of claim 1.

18. A computer, comprising:
a communication module configured to receive an analysis target image that is a specific medical image to compute the bone age, wherein the analysis target image is of bones of entire hand; and
a processor configured to analyze the analysis target image which is received via the communication module using the deep neural network to compute the bone age, and
wherein the deep neural network includes a plurality of convolution layers which create a feature map with respect to features in the analysis target image; and a pooling layer in which a sub-sampling is performed between the plurality of convolution layers, whereby different levels of features are extracted.

* * * * *